United States Patent [19]

Estrada et al.

[11] Patent Number: 5,688,772
[45] Date of Patent: Nov. 18, 1997

[54] QUINOA SAPONIN COMPOSITIONS AND METHODS OF USE

[75] Inventors: Alberto Estrada; Mark J. Redmond; Bernard Laarveld, all of Saskatoon, Canada

[73] Assignee: University of Saskatchewan, Saskatoon, Canada

[21] Appl. No.: 507,843

[22] Filed: Jul. 27, 1995

Related U.S. Application Data

[63] Continuation-in-part of Ser. No. 283,980, Aug. 1, 1994, Pat. No. 5,597,807.

[51] Int. Cl.$^6$ .......................... A61K 31/70; A61K 35/78
[52] U.S. Cl. ................................ 514/25; 424/195.1
[58] Field of Search ........................ 424/195.1; 514/25

[56] References Cited

U.S. PATENT DOCUMENTS

| | | | |
|---|---|---|---|
| 4,501,734 | 2/1985 | Tanaka et al. | 514/198 |
| 4,806,350 | 2/1989 | Gerber | 424/88 |
| 5,057,540 | 10/1991 | Kensil et al. | 514/25 |
| 5,118,671 | 6/1992 | Bombardelli et al. | 514/26 |
| 5,147,859 | 9/1992 | Bombardelli et al. | 514/26 |
| 5,166,139 | 11/1992 | Bombardelli et al. | 514/26 |
| 5,290,557 | 3/1994 | Mason et al. | 424/410 |

FOREIGN PATENT DOCUMENTS

WO88/09336  12/1988  WIPO.
WO91/04052  4/1991  WIPO.
WO93/05789  4/1993  WIPO.

OTHER PUBLICATIONS

R. Bomford, et al., "Adjuvanticity and ISCOM Formation by Structurally Dirverse Sapons", Vaccine 10(9):572–577 1992.

Chem. abstr. vol. 120(3):29681e, Saponins of Quinoa (Chenopodium quinoa): Effects of Processing on Their Abundance in Quinoa Products and Their Biological Effects on Intestinal Mucosal Tissue Jan. 17, 1994.

Chemical Abstracts, 112: 175533j Ma et al., "Additional toxic, bitter saponins from the seeds of Chenopodium quinoa".

International Search Report issued in the corresponding PCT application No. PCT/CA95/00442.

Ma et al., "Additional Toxic, Bitter Saponins from the Seeds of Chenopodium Quinoa," *Journal of Natural Products* 52(5):1132–1135 (Sep. 1989–Oct. 1989).

Gee et al., "Saponins of Quinoa (Chenopodium quinoa): Effects of Processing on their Abundance in Quinoa Products and their biological Effects on Intestinal Mucosal Tissue." *J. Sci. Food Agric.* (1993) 63:201–209.

*Primary Examiner*—John W. Rollins
*Attorney, Agent, or Firm*—Robins & Associates

[57] ABSTRACT

Novel Quinoa saponin pharmaceutical compositions are disclosed. The compositions are useful for enhancing mucosal absorption of a drug administered therewith.

6 Claims, 10 Drawing Sheets

QUINOA SAPONIN COMPOSITIONS AND METHODS OF USE

CROSS-REFERENCE TO RELATED APPLICATION

This application is a continuation-in-part of U.S. patent application Ser. No. 08/283,980, filed Aug. 1, 1994, now U.S. Pat. No. 5,592,807, from which priority is claimed pursuant to 35 USC §120, and which application is incorporated herein by reference in its entirety.

BACKGROUND OF THE INVENTION

1. Technical Field

The present invention relates generally to adjuvants for use in pharmaceutical compositions. In particular, the invention relates to Quinoa saponin adjuvant compositions and methods of using the same.

2. Background of the Invention

Many pharmaceutical compositions include adjuvants in order to increase activity, antigenic potency and to enhance stability of the formulation. For example, absorption adjuvants, such as drug permeation enhancers, are often used to increase topical and mucosal uptake of a coadministered drug. Similarly, immunological adjuvants are used in vaccine compositions to augment cell-mediated and humoral immune responses. Such adjuvants include depot adjuvants, compounds which adsorb and/or precipitate administered antigens and which serve to retain the antigen at the injection site. Typical depot adjuvants include aluminum compounds and water-in-oil emulsions. However, the above-described adjuvants, although increasing antigenicity, often provoke severe persistent local reactions, such as granulomas, abscesses and scarring, when injected subcutaneously or intramuscularly. Other adjuvants, such as lipopolysacharrides and muramyl dipeptides, can elicit pyrogenic responses upon injection and/or Reiter's symptoms (influenza-like symptoms, generalized joint discomfort and sometimes anterior uveitis, arthritis and urethritis). Accordingly, there is a continued need for an effective and safe adjuvant for use in a variety of pharmaceutical compositions and vaccines.

Saponins are glycosidic natural plant products, composed of a ring structure (the aglycone) to which is attached one or more sugar chains. The saponins are grouped together based on several common properties. In particular, saponins are surfactants which display hemolytic activity and form complexes with cholesterol. Although saponins share these properties, they are structurally diverse. In particular, the aglycone can be asteroid, triterpenoid or a steroidalalkaloid and the number of sugars attached to the glycosidic bonds vary greatly.

Saponins have been employed as absorption adjuvants in pharmaceutical compositions. For example, U.S. Pat. No. 4,501,734 describes the use of a triterpenoid saponin extract from *Sapindus mukurossi* Gaertn. to increase absorption of a coadministered β-lactam antibiotic. Saponins have also been used as immunological adjuvants in vaccine compositions against a variety of diseases including protozoal infections and foot and mouth disease. The saponins typically used as immunological adjuvants are triterpene glycosides extracted from the South American tree, *Quillaja saponaria*, termed Quil A. See, e.g., U.S. Pat. No. 5,057,540; International Publication No. WO 88/09336, published 1 Dec. 1988.

Saponins have also been used in pharmaceutical compositions for a variety of other purposes. For example, U.S. Pat. No. 5,118,671 describes the use of aescin, a saponin obtained from *Aesculus hippocastanum* seeds, in pharmaceutical and cosmetic compositions as an anti-inflammatory. Similarly, U.S. Pat. No. 5,147,859 discusses the use of *Glyccyrrhiza glabra* saponin/phospholipid complexes as anti-inflammatory and anti-ulcer agents and U.S. Pat. No. 5,166,139 describes the use of complexes of saponins and aglycons, obtained from *Centella asiatica* and *Terminalia sp.*, with phospholipids in pharmaceutical compositions. International Publication No. WO 91/04052, published 4 Apr. 1991, discusses the use of solid *Quillaja saponaria* saponin/GnRH vaccine compositions for immunocastration and immunospaying.

*Chenopodium quinoa* ("Quinoa") is a grain crop which has been cultivated in South America for a number of years. Fourteen saponins have been characterized from Quinoa which have a single sugar at position 28, and between one and three sugars at position 3 of the aglycone. No therapeutic or medicinal uses for Quinoa saponins have been previously disclosed. Indeed, previous experimenters report that Quinoa saponins lack adjuvanticity (see, e.g., Bomford et al. Vaccine (1992) 10:572–577).

DISCLOSURE OF THE INVENTION

The present invention is based on the surprising discovery that Quinoa saponins are able to act as both immunological and absorption adjuvants to enhance immune responses and mucosal absorption, respectively, to a substance coadministered therewith. The discovery is particularly unexpected in light of the prior art reports that Quinoa saponins lack adjuvant activity. The invention is environmentally desirable because it provides for the use of Quinoa by-products, such as the hulls, which are currently discarded due to the bitterness conferred by the high saponin content.

Accordingly, in one embodiment, the present invention is directed to a pharmaceutical composition comprising at least one Quinoa saponin and a pharmaceutically acceptable vehicle.

In particularly preferred embodiments, the pharmaceutical composition comprises an aqueous Quinoa saponin extract.

In another embodiment, the subject invention is directed to a pharmaceutical composition comprising: (a) an aqueous Quinoa saponin extract; and (b) a selected drug; and (c) a pharmaceutically acceptable vehicle.

Still other embodiments of the subject invention are directed to methods of enhancing mucosal absorption of a selected drug in a vertebrate subject, using the above compositions.

These and other embodiments of the subject invention will readily occur to those of ordinary skill in the art in view of the disclosure herein.

3 saponins (Group 5, open circle); and CTX and two times with Quinoa saponins (Group 7, open square).

Figure 3:
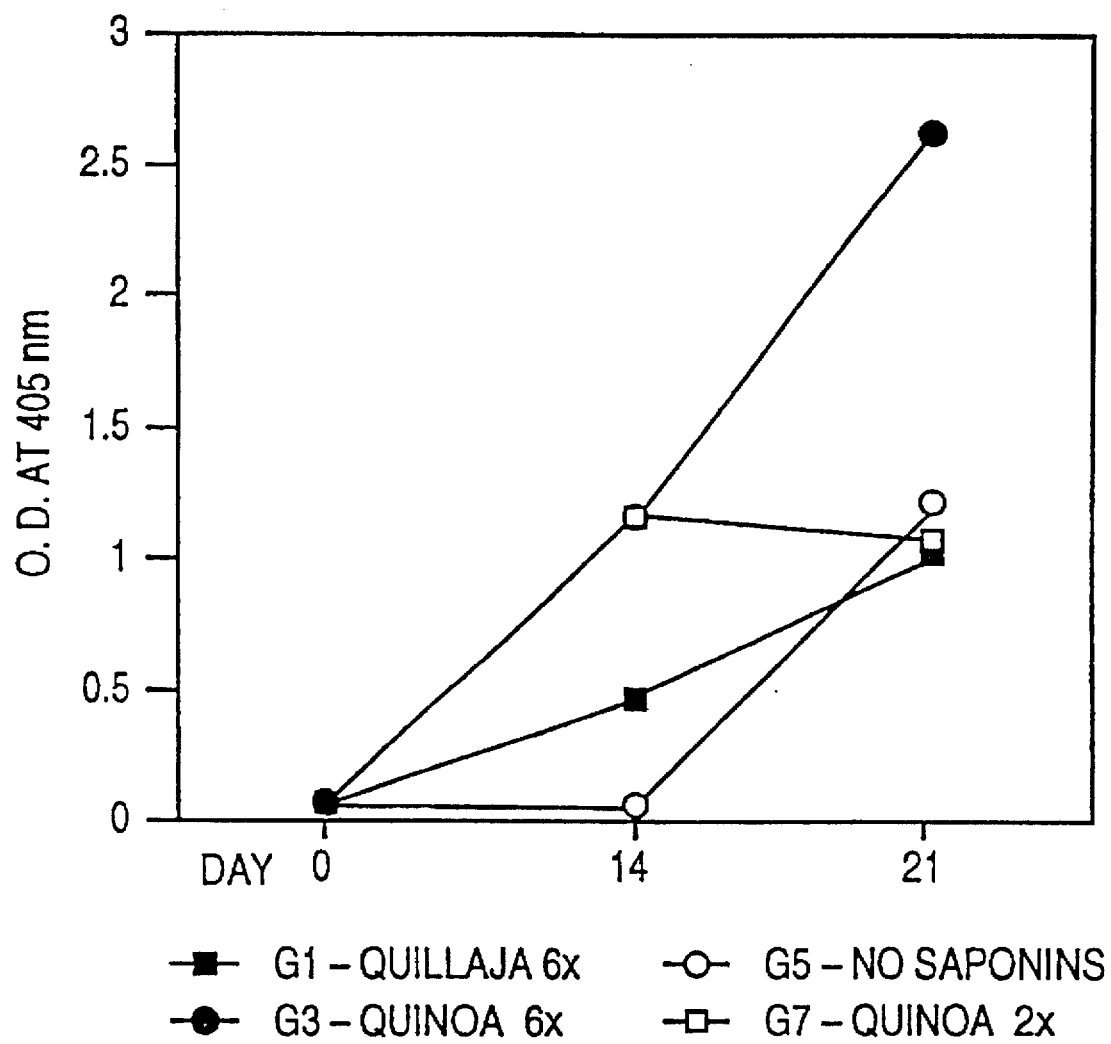

FIG. 3 shows the IgA anti-CTX antibody responses measured in sera (diluted 1:25) obtained from mice immunized orally with CTX and six times with Quillaja saponins (Group 1, solid square); CTX and six times with Quinoa saponins (Group 3, solid circle); CTX with no saponins (Group 5, open circle); and CTX and two times with Quinoa saponins (Group 7, open square).

Figure 4:
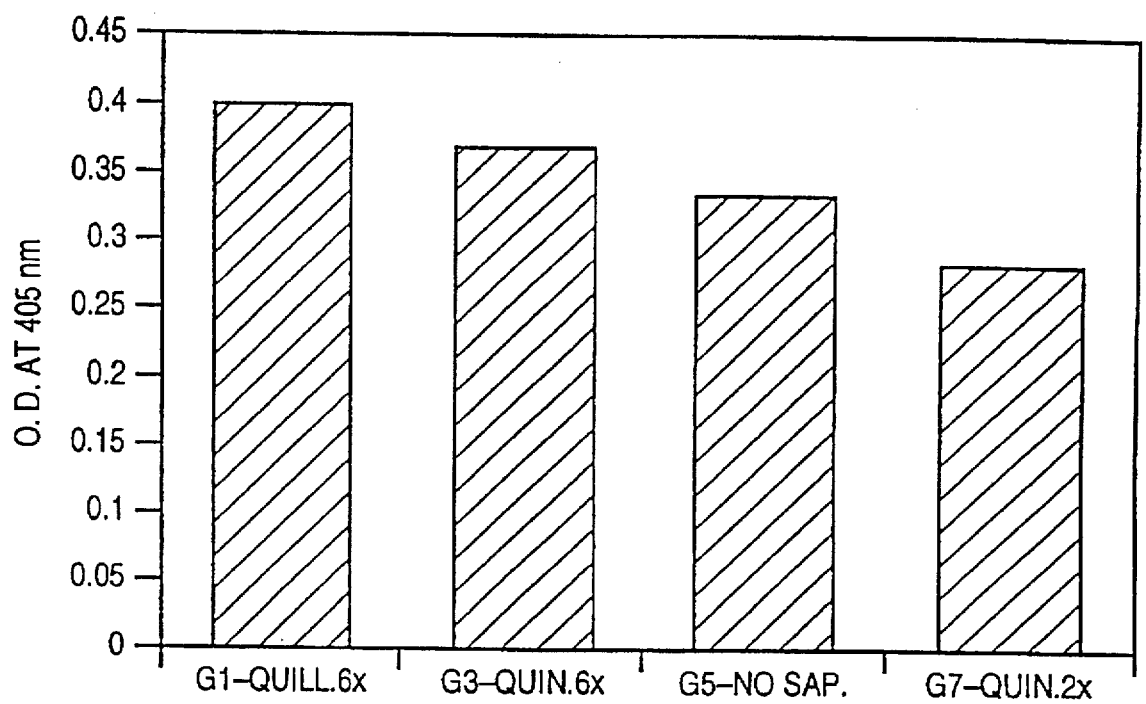

FIG. 4 depicts the IgG anti-CTX antibody responses measured in gut washes (diluted 1:5) obtained from mice immunized orally with CTX and six times with Quillaja saponins; CTX and six times with Quinoa saponins; CTX with no saponins; and CTX and two times with Quinoa saponins.

Figure 5:
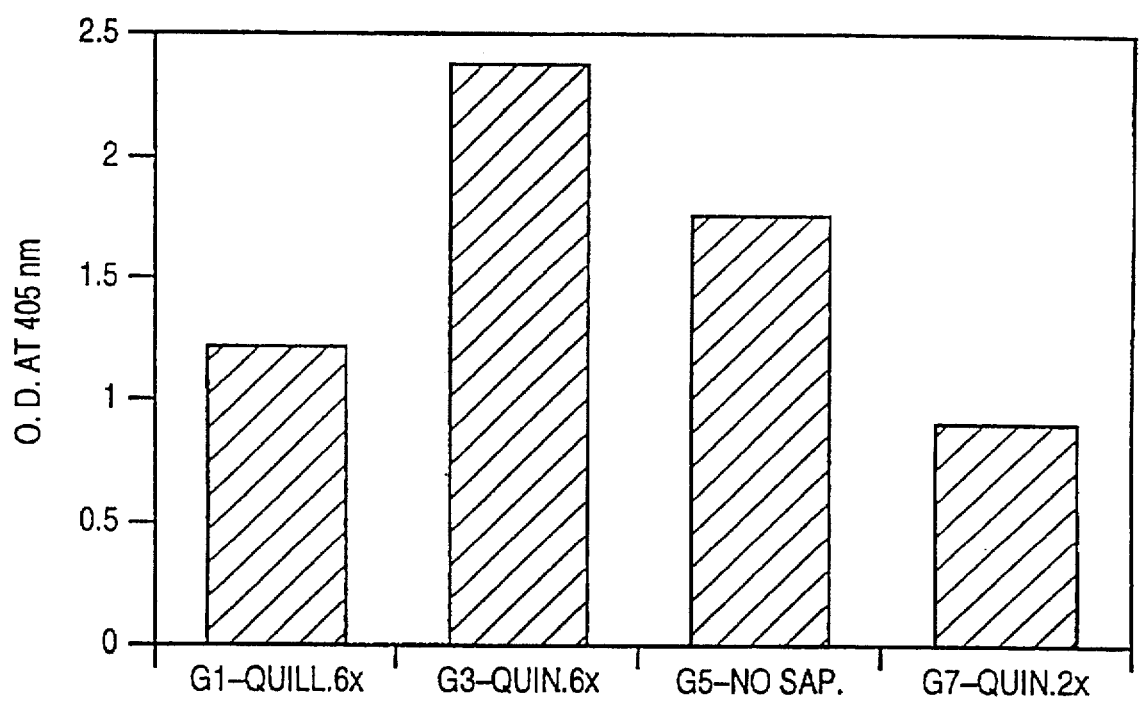

FIG. 5 shows the IgA anti-CTX antibody responses measured in gut washes (diluted 1:5) obtained from mice immunized orally with CTX and six times with Quillaja saponins; CTX and six times with Quinoa saponins; CTX with no saponins; and CTX and two times with Quinoa saponins.

Figure 6:
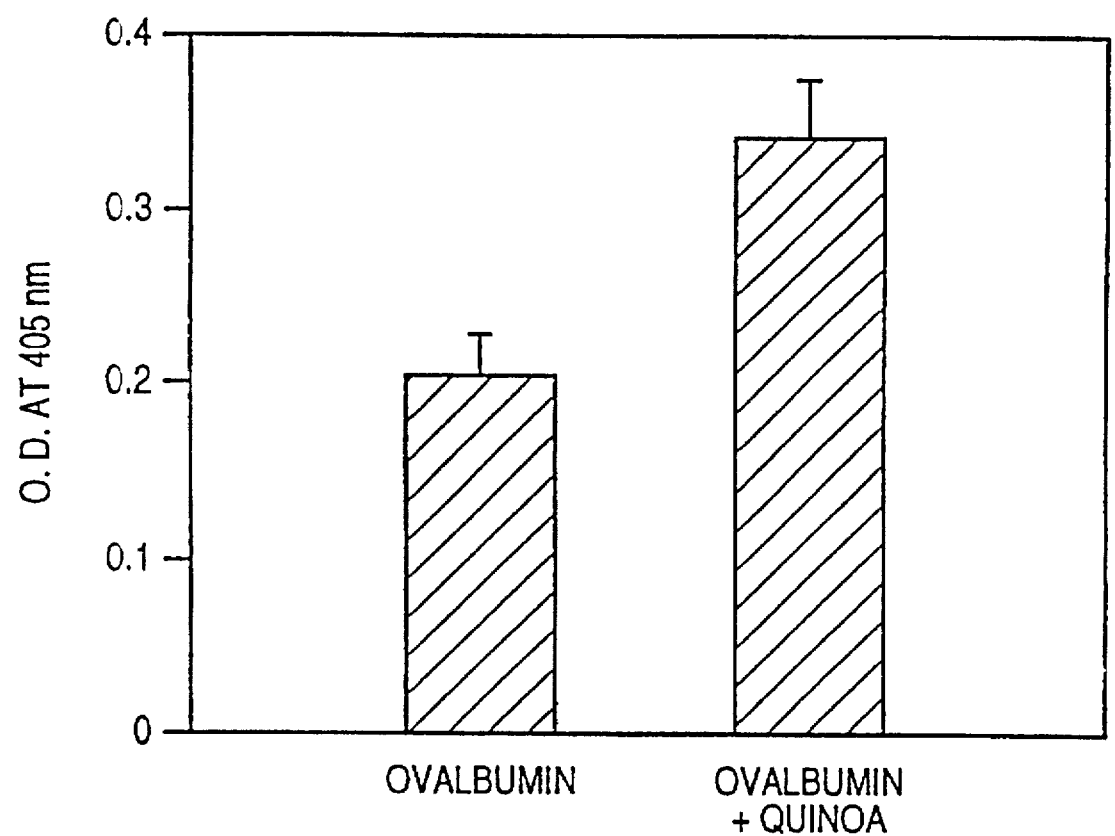

FIG. 6 shows the IgG anti-ovalbumin antibody responses measured in sera (diluted 1:100) obtained from mice immunized subcutaneously three times subcutaneously with ovalbumin; and with ovalbumin plus Quinoa.

Figure 7:
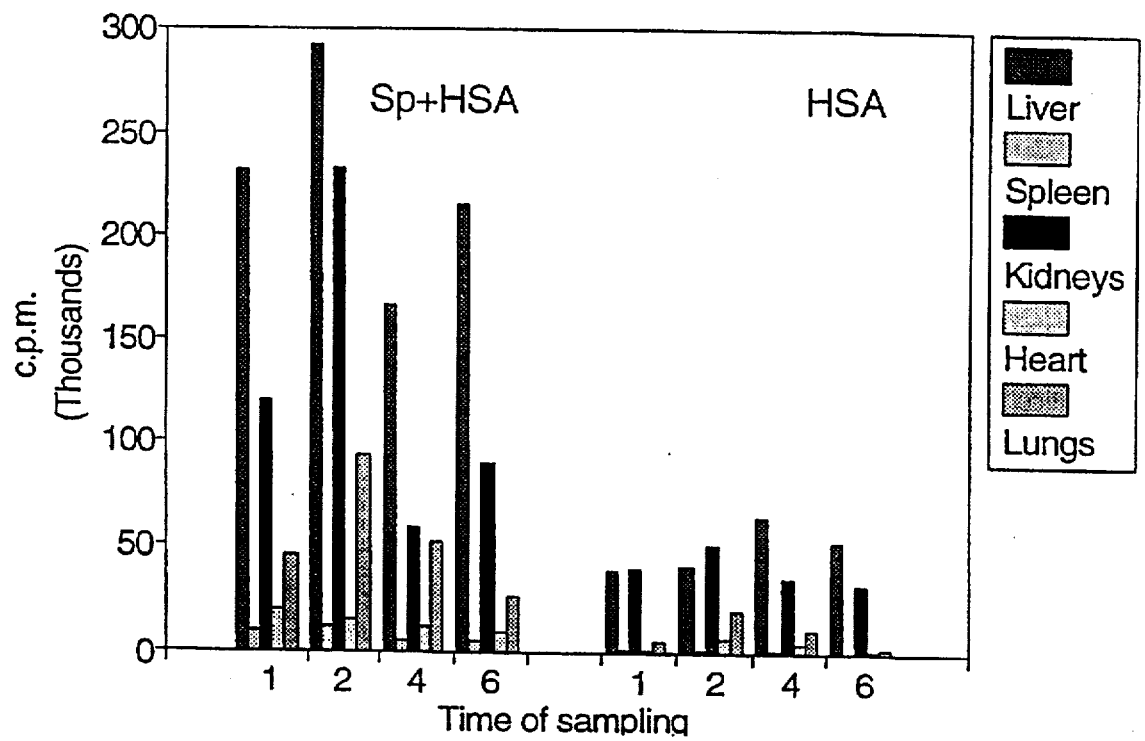

FIG. 7 is a bar graph showing the effect of Quinoa saponins (Sp) on mucosal absorption of radiolabeled human serum albumin (HSA) as assessed by monitoring the presence of labeled HSA in liver, spleen, kidneys, heart and lungs, in the presence and absence of Quinoa saponins. Each point in the figure represents the mean of three mice.

Figure 8A:
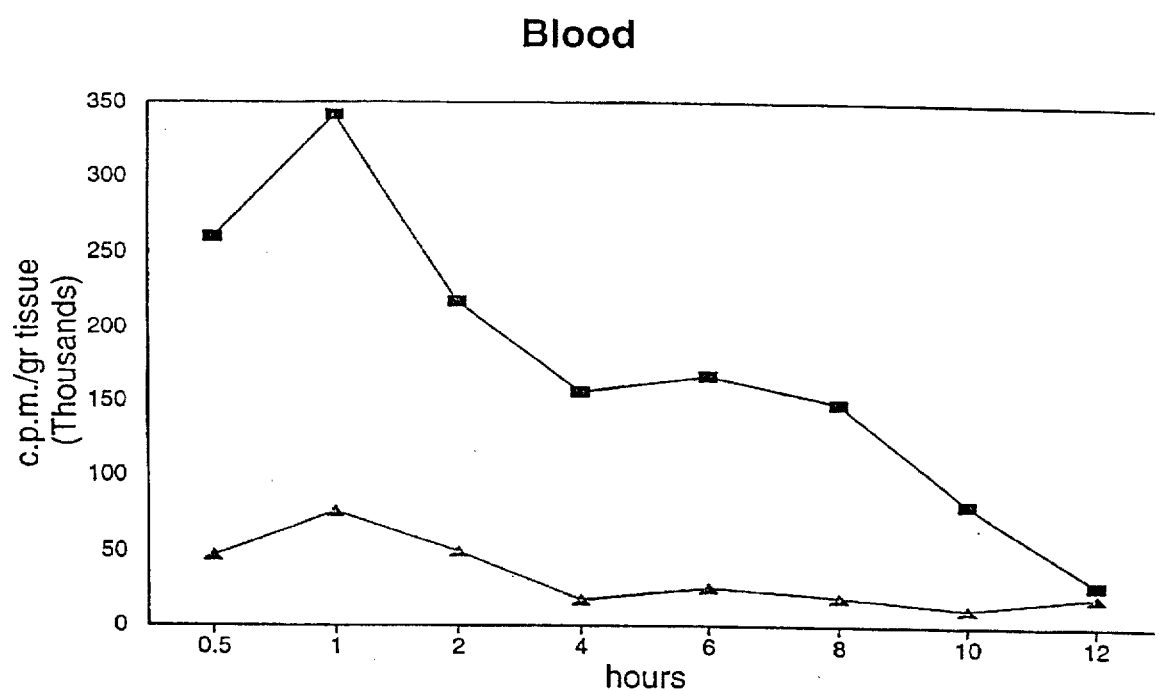
Figure 8B:
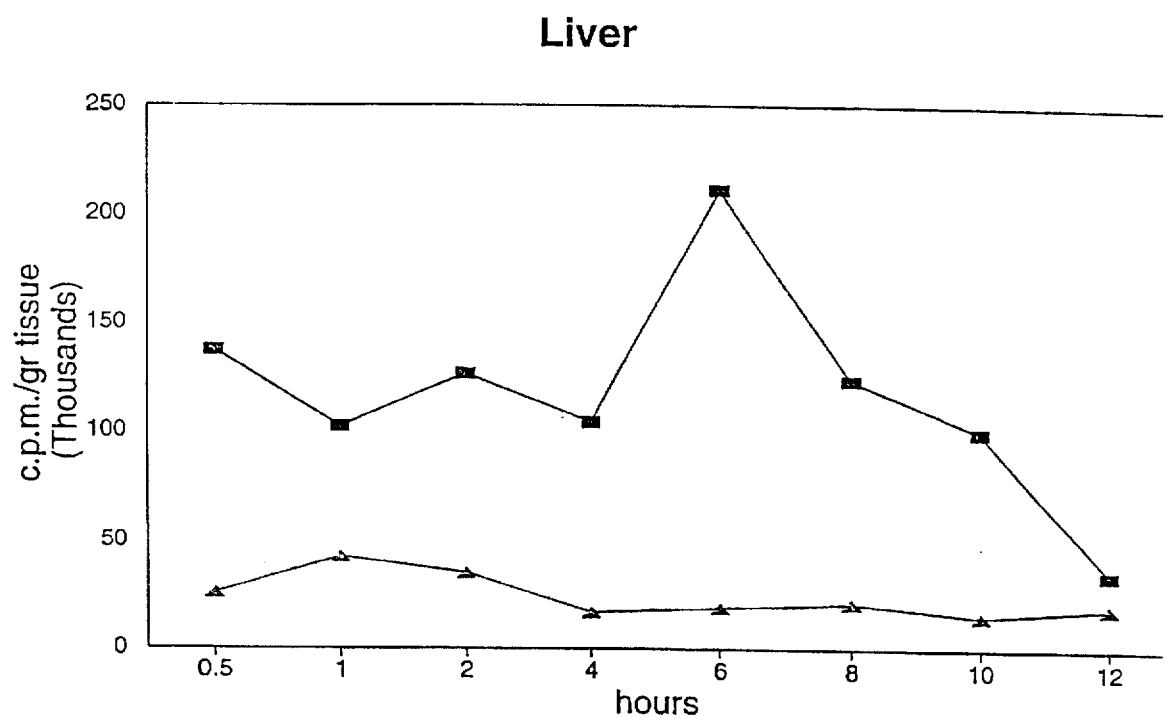
Figure 8C:
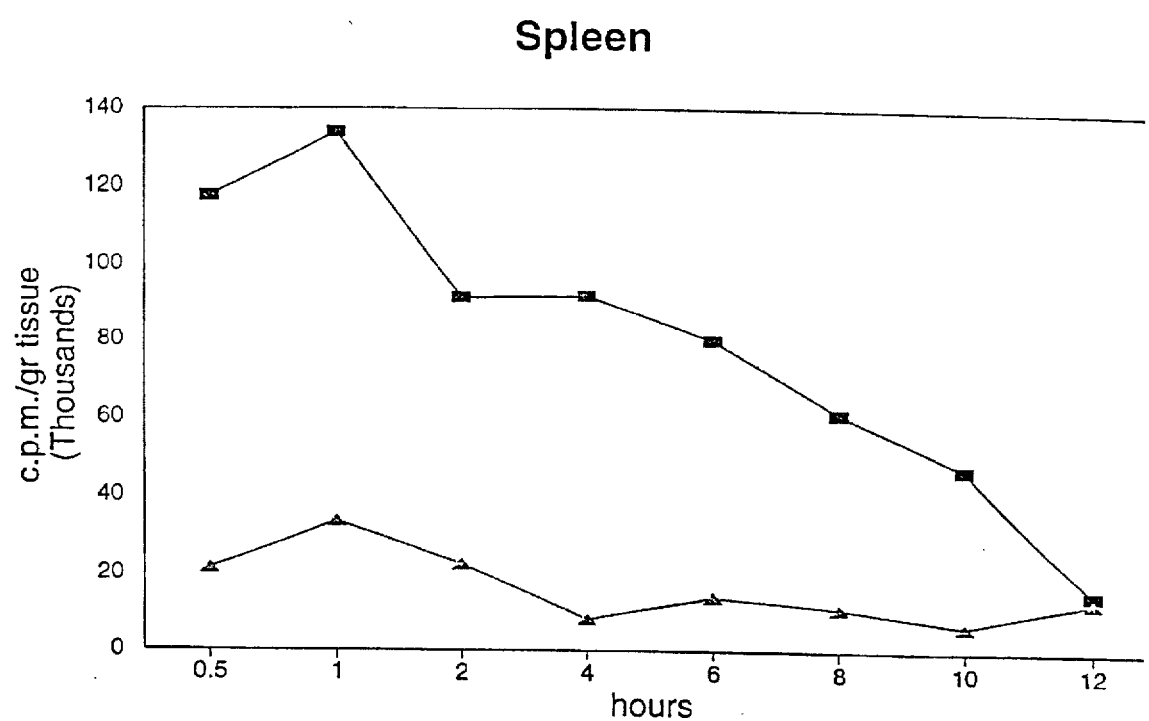

FIGS. 8A–8C show the effect of Quinoa saponins on mucosal absorption of radiolabeled human serum albumin (HSA) as assessed by monitoring the presence of labeled HSA in blood (FIG. 8A); liver (FIG. 8B) and spleen (FIG. 8C), in the presence (■) and absence (solid triangle) of Quinoa saponins. Each point in the figure represents the mean of three mice.

DETAILED DESCRIPTION OF THE INVENTION

The practice of the present invention will employ, unless otherwise indicated, conventional methods of chemistry, biochemistry, immunology and pharmacology, within the skill of the art. Such techniques are explained fully in the literature. See, e.g., *Remington's Pharmaceutical Sciences*, 18th Edition (Easton, Pa.: Mack Publishing Company, 1990); *Methods In Enzymology* (S. Colowick and N. Kaplan, eds., Academic Press, Inc.); and *Handbook of Experimental Immunology*, Vols. I–IV (D. M. Weir and C. C. Blackwell, eds., 1986, Blackwell Scientific Publications).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise. Thus, the term "a saponin" can include more than one saponin or even a crude extract comprising several saponins.

A. Definitions

In describing the present invention, the following terms will be employed, and are intended to be defined as indicated below.

By "Quinoa saponin" is meant any of the various sapogenin glycosides derived from the *Chenopodium quinoa* plant, as well as active fragments and derivatives thereof, which individually or in combination act as absorption and/or immunological adjuvants, for enhancing nonspecific immunity, as well as enhancing the action of a drug or antigen coadministered therewith. The term encompasses crude saponin extracts which contain all or most of the saponins present in Quinoa, as well as partially purified and highly purified saponins derived from the Quinoa plant. The term also encompasses natural and pharmaceutically acceptable salts of the Quinoa saponins. Immunological adjuvant activity of the administered Quinoa saponins can be tested using standard techniques including ELISAs, hemagglutination assays, neutralization assays and the like. Drug enhancement can also be determined using standard techniques, i.e., by dose response curves.

An "antigen" refers to a molecule containing one or more epitopes that will stimulate a host's immune system to make a secretory, humoral and/or cellular immunological response. The term denotes both subunit antigens, i.e., antigens which are separate and discrete from a whole organism with which the antigen is associated in nature, as well as killed, attenuated or inactivated bacteria, viruses, parasites or other microbes. Antibodies such as anti-idiotype antibodies, or fragments thereof, and synthetic peptide mimotopes, which can mimic an antigen or antigenic determinant, are also captured under the definition of antigen as used herein. Similarly, an oligonucleotide or polynucleotide which expresses an antigen or antigenic determinant in vivo, such as in gene therapy and DNA immunization applications, is also included in the definition of antigen herein.

An "immunological response" to a pharmaceutical composition according to the present invention is the development in the host of a secretory, cellular and/or antibody-mediated immune response to the composition of interest. Usually, such a response includes but is not limited to one or more of the following effects; the production of antibodies from any of the immunological classes, such as immunoglobulins A, D, E, G or M; the proliferation of B and T lymphocytes; the provision of activation, growth and differentiation signals to immunological cells; expansion of helper T cell, suppressor T cell, and/or cytotoxic T cell and/or γδT cell populations. Generally, the foregoing events will be substantially directed toward an antigen or antigens included in the composition of interest. However, as described further below, the saponin compositions of the present invention can also be used to enhance nonspecific immunostimulatory activity and such is included in the definition of "immunological response" as used herein.

An "immunological adjuvant" refers to a Quinoa saponin or a Quinoa saponin extract which potentiates an immunological response in the subject to which it is administered. The Quinoa saponin can be incorporated into or administered with the antigen or administered in a separate composition. Alternatively, the Quinoa saponin can be administered without an accompanying antigen to stimulate nonspecific immunity. An immunological adjuvant may enhance the immunological response by making the antigen more strongly immunogenic or by lowering the dose of antigen necessary to achieve an immune response in the subject to which it is administered.

An "absorption adjuvant" refers to a Quinoa saponin which enhances the absorption of an accompanying substance, such as a drug, in the host to which it is administered. The Quinoa saponin can be incorporated into or administered with the substance of interest either in the same composition or in a separate composition which is delivered either simultaneously, prior to or subsequent to administration of the substance of interest. Generally, absorption will be enhanced through mucosal membranes in vertebrate subjects. However, the Quinoa saponin compositions will also be useful to enhance permeability through plant and insect membranes, e.g., for increasing the uptake of herbicides and fertilizers through the leaves and roots in plants and for enhancing the uptake of pesticides and other insecticides, including bacteria, in insects, such as by permeabilization of cells of the trachea or other membranes.

A pharmaceutical composition which contains the Quinoa saponins and a selected antigen pursuant to the present invention displays "enhanced immunogenicity" when it possesses a greater capacity to elicit an immune response than the immune response elicited by the corresponding antigen when administered alone, without the Quinoa saponins. Such enhanced immunogenicity can be determined by administering the saponin composition and antigen controls to animals and comparing antibody titers against the two using standard assays such as radioimmunoassay and ELISAs, well known in the art.

The term "extract" as used herein refers to both liquid and solid forms (e.g., by the elimination of the solvent) of one or more of the Quinoa saponins.

For purposes of the present invention, an "effective amount" of a Quinoa saponin will be that amount which enhances an immune response to a coadministered antigen, or an amount of a Quinoa saponin which stimulates nonspecific immunity when no antigen is present, or an amount of a Quinoa saponin which increases absorption of a coadministered substance of interest.

By "pharmaceutically acceptable" is meant a material which is not biologically or otherwise undesirable, i.e., the material may be administered to an individual along with the selected adjuvant formulation without causing any undesirable biological effects or interacting in a deleterious manner with any of the components of the pharmaceutical composition in which it is contained.

By "vertebrate subject" is meant any member of the subphylum chordata, including, without limitation, mammals such as cattle, sheep, pigs, goats, horses, and humans; domestic animals such as dogs and cats; and birds, including domestic, wild and game birds such as cocks and hens including chickens, turkeys and other gallinaceous birds. The term does not denote a particular age. Thus, both adult and newborn animals are intended to be covered.

B. General Methods

Central to the present invention is the discovery that Quinoa saponin compositions can promote production of immunoglobulin G (IgG) and immunoglobulin A (IgA) antibodies and enhance both humoral and secretory immune responses in a vertebrate subject when administered with a selected antigen. Additionally, the Quinoa saponins enhance nonspecific immunity and cause increased absorption through mucosal membranes.

Secretory immunity is thought to be largely mediated by IgA antibodies. In particular, secretory IgA serves to block the action of antigens that colonize mucosal surfaces. Thus, IgA plays a significant role in resistance to reinfection by pathogens, such as viruses, which replicate in mucosal membranes, especially those in the gastrointestinal and upper respiratory tract. Such organisms include rhinoviruses, influenza viruses, coronaviruses, parainfluenza viruses, respiratory syncytial virus, herpesviruses, adenoviruses, rhabdoviruses, paramyxoviruses, orthomyxoviruses, rotaviruses and Norwalk-like viruses. Additionally, IgA blocks the action of a number of gram positive and gram negative bacteria, parasites and protozoa, including such microbes as Salmonella, campylobacteria, cryptosporidium, isospora, Eimeria, helminths, and the like.

Similarly, IgA can prevent the passage of organisms through mucosal surfaces to the systemic circulation. This is of particular importance with bacteria, a number of which penetrate through damaged tissue and can cause bacteremia. Examples of organisms which initially infect mucosal surfaces and then pass into the systemic circulation include those bacteria and viruses described above, as well as the picornaviruses, poxviruses, flaviviruses, orbiviruses and alphaviruses. Serum antibodies, such as IgG, often do not provide protection of the mucosal surfaces.

Systemic antibodies, such as serum IgG, however, do play a significant role in neutralizing infectivity of invading organisms and promoting aggregation and clearance of pathogens, such as viruses that have a viremic mode of spread. Thus, the ability of the Quinoa saponins to augment both IgG and IgA production against selected antigens provides a powerful tool against infection by a wide variety of organisms.

Accordingly, as is evident, the Quinoa saponins can be used as immunological adjuvants in vaccine compositions for a variety of purposes. For example, the Quinoa saponins can be used in compositions for immunizing a vertebrate subject against a selected pathogen or against a subunit antigen derived therefrom, or for priming an immune response to a particular antigen or, for example, stimulating an immune response against a desired hormone for e.g., reproductive purposes such as fertility control and immunological sterilization. The compositions can also be used to stimulate nonspecific immunity. If used for this purpose, a specific antigen need not be present or coadministered with the Quinoa saponin adjuvants.

Antigens, when administered with the Quinoa pharmaceutical compositions, can be derived from a wide variety of viruses, bacteria, fungi, plants, protozoans and other parasites. Such antigens can be derived from, e.g., any of the various species of Pasteurella, Actinobacillus, Haemophilus, Salmonella, Eimeria, and the like, as well as those viruses specified above, including, e.g., rotaviruses (including canine, feline, bovine, porcine, equine and human rotaviruses), herpesviruses such as BHV-1, EHV-1, PRV, Parvovirus, rabiesvirus, influenza viruses (including canine, feline, bovine, porcine, equine and human influenza), parainfluenza viruses (also including canine, feline, bovine, porcine, equine and human parainfluenza), hepatitis viruses, HIV, coronaviruses (including canine, feline, bovine, porcine, equine and human coronaviruses), and the like. Similarly, antibody responses to tumor antigens, hormones, hormone analogs, and so forth, will also be enhanced by use of the Quinoa compositions herein described.

The antigen can be a protein, polypeptide, antigenic protein fragment, oligosaccharide, polysaccharide, or the like. Similarly, an oligonucleotide or polynucleotide, encoding a desired antigen, can be administered with the Quinoa saponin adjuvants for in vivo expression. In particular, the increased mucosal absorption caused by the saponin compositions aids the uptake of DNA into cells and nuclei and hence increases the efficiency of DNA immunization.

Antibodies such as anti-idiotype antibodies, or fragments thereof, can also be used in conjunction with the Quinoa adjuvants. Furthermore, the Quinoa adjuvants can be used in combination with antibodies for passive immunization.

The Quinoa saponins can also be used as absorption adjuvants, to enhance the uptake of a substance, such as a drug, administered therewith, through e.g., mucosal surfaces including membranes of the mouth, intestine, rectum, nose, eye and lung, among others. Drugs that will benefit from such absorption enhancers include antibiotics, anti-arythmics, anti-cancer compounds, stimulants, relaxants, as well as nutrients and nutrient supplements, sugars, oils, vitamins, minerals, proteins and amino acids. The Quinoa saponins will also serve to increase absorption through plant and insect cells, as explained above.

The Quinoa saponin pharmaceutical compositions will often contain the antigen or drug of interest, either free or complexed to the saponin, as described in European Patent Application No. 244,719, published 11 Nov. 1987 and International Publication No. WO 93/05789, published 1 Apr. 1993. However, the antigen or drug need not be present in the saponin composition but can be administered separately, either simultaneously, just prior to or subsequent to the saponin composition.

Quinoa saponins for use in the pharmaceutical compositions of the present invention can be purified from the *Chenopodium quinoa* plant using methods well known in the art. See, e.g., U.S. Pat. Nos. 5,057,540 and 4,501,734, as well as International Publication Nos. WO 88/09336, published 1 Dec. 1988 and WO 93/05789, published 1 Apr. 1993. A particularly preferred method for obtaining saponins from Quinoa involves a water extraction of Quinoa hulls, as described in the examples. The extracted saponins can be used as is or further purified using such techniques as column chromatography, HPLC, immunoadsorbent techniques, affinity chromatography and immunoprecipitation.

Following extraction of the Quinoa saponins, it may be desirable to complex the saponins with a sterol and, optionally, a phospholipid, to produce immunostimulating complexes known in the art as ISCOMs. ISCOMs have been shown to enhance absorption, pharmacological activity and tolerability of saponin adjuvants. Useful sterols include, for example, cholesterol, β-sitosterol, lanosterol, lumisterol, stigmasterol and sitosterol. Useful phospholipids include, for example, phosphatidic acid and esters thereof including phosphatidylcholine and phosphatidylethanolamine. Methods for producing ISCOMs are known in the art and described in e.g., U.S. Pat. No. 5,118,671, U.S. Pat. No. 4,900,549, International Publication No. WO 90/03184 and Bomford et al. Vaccine (1992) 10:572–577.

The Quinoa saponins, in the form of a crude extract, a more purified product, or as ISCOMs, are then formulated into pharmaceutical compositions. Such compositions will contain an effective amount (as defined above) of the Quinoa saponins. The appropriate amount of the saponins to be administered will depend on the mode of administration and can be readily determined by one skilled in the art based on activity assays of the preparations, such as hemolytic activity assays, as described in the examples. For example, if the compositions are administered subcutaneously and hemolytic assays are used to assay activity, generally, from about 0.1 to about 1000 hemolytic units (HU) will be delivered, more particularly from about 1 to about 100 HU and most preferably from about 5 to about 50 HU. For oral delivery, generally from about 10 to about 100,000 HU, more preferably about 100 to about 10,000, most preferably 500 to about 5000, will be administered. Doses for other modes of adminstration can be readily determined by one of skill in the art.

The Quinoa saponin compositions will generally include a compatible pharmaceutical vehicle, such as, for example, water, saline, dextrose, glycerol, ethanol, or the like, and combinations thereof. The pharmaceutical compositions may additionally contain biological buffers, preservatives, wetting and emulsifying agents, and the like. The formulations may also include other adjuvants, in addition to the Quinoa saponins, including for example, muramyl dipeptides, avridine, aluminum hydroxide, oils, cytokines, and other substances known in the art.

As explained above, the Quinoa saponin compositions may or may not contain an antigen or other substance of interest. For example, formulations may be administered without an antigen, so as to induce a nonspecific immunostimulatory response. Similarly, an antigen or drug composition can be administered separately from the Quinoa saponin compositions. A selected antigen, if included in the composition, will be present on the order of about 0.1 µg to about 1000 µg, more preferably about 1 µg to about 100 µg. Other amounts which are effective for eliciting an immune response will also be useful in the present compositions. If a drug is included in the composition, the amount present will depend on the type of drug used and is readily determined by one of skill in the art.

Some antigens or drugs will benefit by being coupled with a carrier molecule. This is particularly true of small peptides, such as small peptide hormones or substances with short half-lives and poor immunogenicity. Suitable carriers include large, slowly metabolized macromolecules such as proteins, including serum albumins, keyhole limpet hemocyanin, immunoglobulin molecules, thyroglobulin, ovalbumin, and other proteins well known to those skilled in the art; polysaccharides, such as sepharose, agarose, cellulose, cellulose beads and the like; polymeric amino acids such as polyglutamic acid, polylysine, and the like; amino acid copolymers; inactive virus particles; and polynucleotides.

The mode of administration of the Quinoa saponin compositions will vary according to the intended use. For example, if used as immunological adjuvants (e.g., in the case of a vaccine) and systemic immunity is required, the Quinoa saponin compositions will generally be administered parenterally, usually by intramuscular injection. If mucosal immunity is required, the Quinoa saponin will generally be adminstered enterally, usually by oral dosing or inhalation. Other modes of administration, however, such as intradermal, intraperitoneal and intravenous injection, are also acceptable. The subject is immunized by administration of at least one dose, and preferably two or more doses. Moreover, the subject may be administered as many doses as is required to enhance immunity to the pathogen in question.

When used as absorption adjuvants, the subject compositions will generally be delivered by oral, intranasal, topical, rectal, intraocular and inhalation methods, and the like. However, such compositions can also be administered subcutaneously, intramuscularly, intradermally, and intraperitoneally. Dosing will depend on the drug administered and the disorder in question but will generally follow a regimen of one to several doses per day for several days, weeks or months.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

C. Experimental

Materials and Methods

Saponins

*Quillaja saponaria* saponin was obtained from Sigma Chemical Co. (St. Louis, Mo.). Quinoa saponin was extracted from *Chenopodium quinoa* seeds. For the extraction, 100 ml of distilled water were added to 10 g of quinoa hulls and kept under agitation using a stirring bar for 30 min. The mixture was then centrifuged at 2,500 rpm for 15 min and the supernatant collected. 100 ml of distilled water were added to the pellet and the procedure repeated. The supernatants collected were freeze-dried and stored at 18° C.

Saponins activity assay

Since saponins are known to lyse red blood cells, a hemolytic test was used to test the activity of the Quillaja and Quinoa saponins. In particular, 100 µl of 1% sheep red blood cells in phosphate buffered saline (PBS) were added to individual wells of a 96 well microtiter plate. 1 mg of the Quillaja and Quinoa saponins in PBS were added to the top wells and 2× serial dilutions performed. The saponin content was estimated as the last dilution showing complete hemolysis of the red cells and expressed as hemolytic units (HU) per mg of material. Quillaja saponins had 256 HU/mg whereas the Quinoa extract presented 64 HU/mg. The administration of both saponins to mice was standardized on basis of their HU.

Animals

Female BALB/C and female CD1 mice were obtained from the Animal Resources Center University of Saskatchewan (Saskatoon, Canada). The BALB/C mice were 6 weeks of age when first used and the CD1 mice were 8 weeks of age when first used.

EXAMPLE I

Adjuvant Activity of Quinoa Saponins

To examine the adjuvant activities of the Quillaja and Quinoa saponins in vivo, cholera toxin (CTX) from List Biological Laboratories (Campbell, Calif.) and avidin from Sigma (St. Louis, Mo.) were used as model antigens. Mice were immunized by the oral and subcutaneous (S.C.) routes, respectively. The immunization protocol is depicted in Table 1.

Blood samples were obtained from the mice on days 7, 14, and 21 days post primary immunization. The blood was centrifuged at 1000 g for 20 minutes and the serum removed, aliquoted and stored at −20° C. before analysis by ELISA.

Intestinal washings were collected from the immunized mice by everting the entire small intestine over a capillary tube and rinsing the intestinal mucosa with 5 ml of PBS containing 0.05 TIU/ml Aprotinin, 2 mM phenylmethylsulfonyl fluoride, 5 mM ethylene diamine tetraacetic acid and 0.02% $NaN_2$ for 4 h at 4° C. All samples were clarified by centrifugation and stored at −20°C. until analysis by ELISA.

An ELISA was used to measure anti-avidin IgG in sera and anti-CTX IgG and IgA antibody titres in sera and gut washes. Specifically, microtiter plate wells (Immuno Plate; Nunc, Inter-Med, Denmark) were coated for 17 hours with 2 µg of avidin or with 1 µg CTX in PBS at 4° C. The plates were then washed with Tris buffer containing 0.05% Tween-20 (Tris-Tween) and incubated with 1% bovine serum albumin (Sigma) in PBS for 60 min at 37° C. The wells were washed three times with Tris-Tween. Serum dilutions of 1:100 for the detection of IgG antibodies anti-avidin, 1:50 for IgG anti-CTX antibodies and 1:25 for IgA anti-CTX antibodies were performed. For the detection of IgG and IgA anti-CTX in gut washes, the samples were diluted 1:5. The antibodies were incubated in the wells for 2 h at 37° C. The wells were then washed with Tris-Tween. Alkaline phosphatase-conjugated goat anti-mouse IgG or IgA antibodies (Southern Biotechnology Associates, Birmingham, Ala.) were diluted 1:1000 with Tris-Tween and 100 µl of the diluted conjugate added to each well and incubated at 37° C. for 60 min. The wells were washed with Tris-Tween and 100 µl of a substrate solution consisting of 1 mg/ml of p-nitrophenyl phosphate (104 phosphatase substrate tablets; Sigma) in 1.0M diethanolamine buffer, pH 9.8 were added to each well. The absorbance of each well at 405 nm was determined. Antibody titres were determined by measuring the optical density (O.D.) readings at a wavelength of 405 nm using an automated spectrophotometer (Kinetic Microplate Reader, Molecular Devices, Menlo Park, Calif.).

TABLE 1

Saponins administration to mice by oral and subcutaneous routes

| | | | | | Experimental days | | | | | |
|---|---|---|---|---|---|---|---|---|---|---|
| Group No. | Saponin | Route | Antigen | Route | 0 | 3 | 7 | 10 | 14 | 17 | 21 |
| 1 | Quillaja | Oral | CTX | Oral | * | * | * | * | * | * | |
| 2 | Quillaja | S.C. | Avidin | S.C. | ** | | | | ** | | |
| 3 | Quinoa | Oral | CTX | Oral | * | * | * | * | * | * | |
| 4 | Quinoa | S.C. | Avidin | S.C. | ** | | | | ** | | |
| 5 | * | * | CTX | Oral | | | | | | | |
| 6 | * | * | Avidin | S.C. | | | | | | | |
| 7 | Quinoa | Oral | CTX | Oral | * | | | | * | | |
| | | | | | Vaccine | | | | Bleed Boost | | Bleed Sample |

Figure 1:
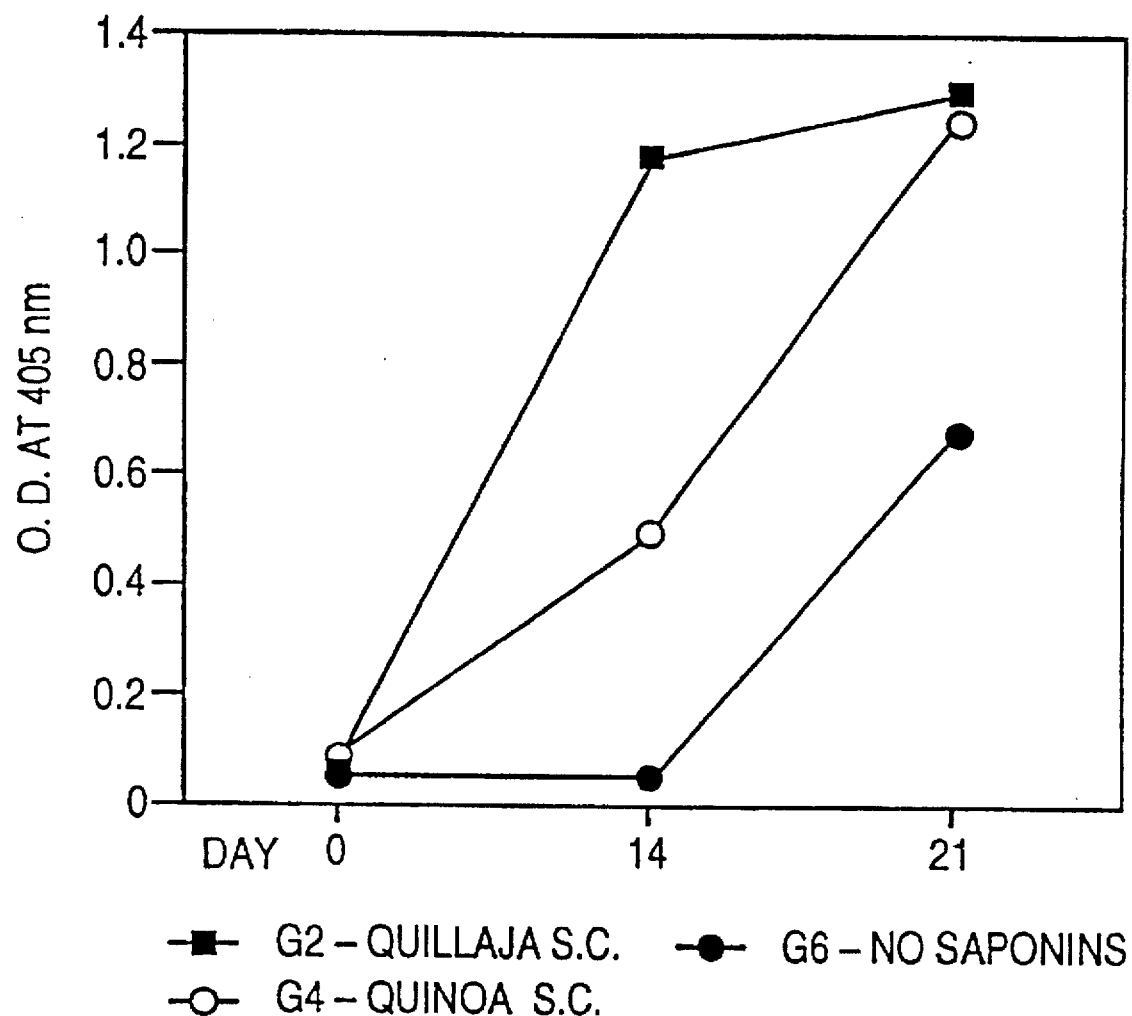
FIG. 1 depicts the IgG anti-avidin responses measured in sera (diluted 1:100) obtained from mice immunized subcutaneously (S.C.) with avidin and Quillaja saponins (Group 2, solid square), avidin and Quinoa saponins (Group 4, open circle), and avidin with no saponins (Group 6, solid circle). The Group designations are as specified in Table 1.

5 mice/group
Saponins:
Quillaja:
*Oral - 10 mg/mouse (given 4 hrs. before vaccination)
**S.C. - 100 µg/mouse
Quinoa:
*Oral - 40 mg/mouse (given 4 hrs. before vaccination)
**S.C. - 400 µg/mouse
Antigens:
CTX - 2 µg/mouse 5 mice/group
Avidin - 100 µg/mouse As can be seen in FIG. 1, the primary immune response, measured on day 14, was higher for the groups which had been administered saponin adjuvants, with the Quillaja saponin adjuvant inducing a higher IgG response to avidin. The secondary immune response, measured on day 21, indicated that IgG responses were equivalent in magnitude for both the Quinoa and Quillaja saponin adjuvants.

Figure 2:
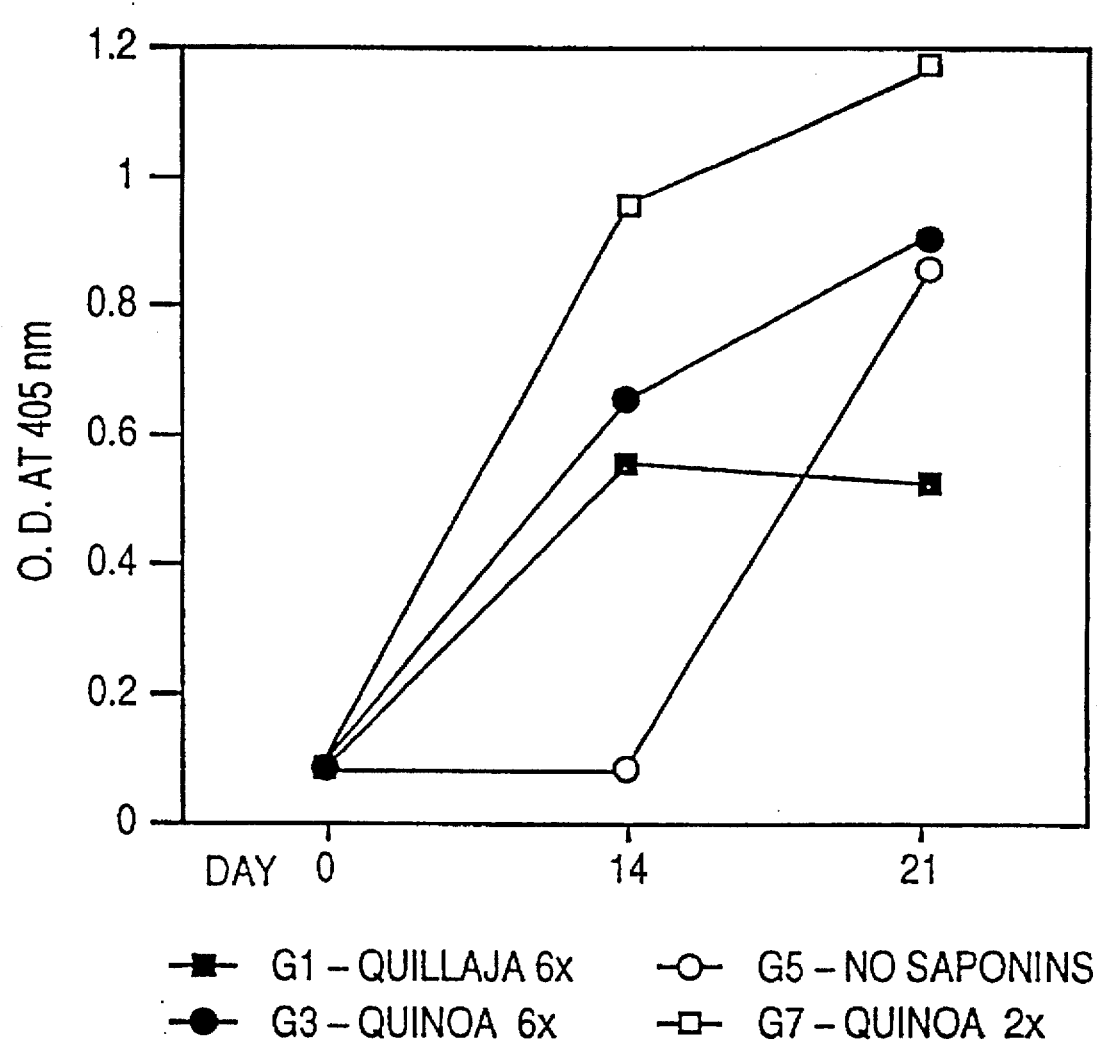
FIG. 2 shows the IgG anti-cholera toxin (CTX) antibody responses measured in sera (diluted 1:50) obtained from mice immunized orally with CTX and six times with Quillaja saponins (Group 1, solid square); CTX and six times with Quinoa saponins (Group 3, solid circle); CTX with no

FIGS. 2 and 3 show that the administration of Quinoa saponins induced higher primary serum IgG and responses to CTX than the administration of Quillaja saponins or the antigen alone. The group 2 animals that received Quinoa saponins a total of six times were found to have a strong secondary response to the antigen. This may be due to an increase in gut permeability caused by the Quinoa saponin adjuvant.

FIGS. 4 and 5 show that oral administration of CTX together with either Quillaja or Quinoa saponins, followed by two additional saponin treatments 3 and 6 days later, induced a higher IgG intestinal response to the antigen. The administration of Quinoa saponins a total of six times induced the highest intestinal IgA response. Intestinal immune responses are of importance to protection against disease since many infectious organisms either colonize the mucosa of the intestine and the lung or gain access to the systemic circulation through these surfaces. Secretory IgA are the primary defense mechanism of the gut. Such IgA responses have not heretofore been reported for Quillaja.

In order to confirm that the Quinoa saponin adjuvant compositions were indeed able to stimulate an anti-IgG response when administered subcutaneously, an additional experiment was done using ovalbumin as the antigen. In particular, ovalbumin from Sigma (St. Louis, Mo.) was used to immunize mice by the subcutaneous route. Mice were immunized on days 0, 7 and 14 with 100 µg of ovalbumin or ovalbumin formulated with the Quinoa saponins. Serum samples were obtained from the animals on day 21 and anti-ovalbumin IgG measured by an ELISA. As can be seen in FIG. 6, the animals that received the vaccine containing the Quinoa saponins showed significantly higher antibody titers than the animals that received ovalbumin without the Quinoa saponins.

EXAMPLE II

Enhanced Absorption Using Quinoa Compositions

This example shows the effect of Quinoa saponins on mucosal absorption of a coadministered drug. The effect was evaluated by following the mucosal uptake and biodistribution of radiolabelled antigen and proceeded as follows.

Human Serum Albumin (HSA) (Sigma Chemical Co., St. Louis, Mo.) was radiolabelled with Technetium ($^{99m}$Tc). HSA (1 mg) was incubated with 5 mCi of $^{99m}$Tc for 30 min at 25° C. Free radiolabel was removed by thin layer-paper chromatography using a saline solution as running buffer. A saponin preparation from *Chenopodium quinoa* was extracted as described above and used without further processing.

100 µl of an antigen-saponin preparation was administered to CD1 mice by an oral-gastric route using a 100 µl pipette fitted with a blunt-ended needle.

a. In one experiment which included 12 mice per group, mice were administered 100 µl of the antigen-saponin preparation which included 0.2M NaHCO$_3$ solution containing 40 mg (2560 HU) of saponins (Sp) and 100 µCi of $^{99m}$Tc-HSA (group 1-Sp+$^{99m}$Tc-HSA) or radiolabelled HSA alone (group 2-control $^{99m}$Tc-HSA).

Three mice from each group were euthanized at each time point, as shown in FIG. 7. Liver, spleen, kidney, heart and lung tissue samples were collected and evaluated by measuring radioactivity in the samples using a γ-counter. As shown in FIG. 7, the presence of Quinoa saponins in the preparation dramatically increased the levels of HSA in the tissue samples, indicating increased mucosal absorption of the preparation.

b. Since the results of the previous experiment were so dramatic, an experiment was conducted using half the amount of Quinoa saponins as follows. Mice (24 per group) were administered an HSA-saponin preparation as above but with 20 mg (1280 HU) of Quinoa saponins in the preparation. Three mice from each group were euthanized at the time points shown in FIGS. 8A–8C and blood, liver and spleen samples collected. The radioactivity in the samples was measured as above. As shown in FIGS. 8A–8C, even the reduced dose of Quinoa saponins dramatically increased the levels of HSA found in blood (FIG. 8A), liver (FIG. 8B) and spleen (FIG. 8C).

Thus, novel Quinoa saponin compositions and methods for using the same are disclosed. Although preferred embodiments of the subject invention have been described in some detail, it is understood that obvious variations can be made without departing from the spirit and the scope of the invention as defined by the appended claims.

We claim:

1. A pharmaceutical composition comprising at least one Quinoa saponin; a selected drug; and a pharmaceutically acceptable vehicle.

2. The composition of claim 1, wherein said at least one Quinoa saponin comprises an aqueous Quinoa saponin extract.

3. A pharmaceutical composition comprising:

(a) an aqueous Quinoa saponin extract; and (b) a selected drug; and (c) a pharmaceutically acceptable vehicle.

4. A method for enhancing mucosal absorption of a selected drug in a vertebrate subject, said method comprising administering an effective amount of the pharmaceutical composition of claim 1, to said subject.

5. A method for enhancing mucosal absorption of a selected drug in a vertebrate subject, said method comprising administering an effective amount of the pharmaceutical composition of claim 2, to said subject.

6. A method for enhancing mucosal absorption of a selected drug in a vertebrate subject, said method comprising administering an effective amount of the pharmaceutical composition of claim 3, to said subject.

* * * * *